United States Patent
Fernandez et al.

(10) Patent No.: US 8,575,352 B2
(45) Date of Patent: Nov. 5, 2013

(54) BENZYL SULFONAMIDE DERIVATIVES USEFUL AS MOGAT-2 INHIBITORS

(71) Applicant: Eli Lilly and Company, Indianapolis, IN (US)

(72) Inventors: Maria Carmen Fernandez, Madrid (ES); Lance Allen Pfeifer, Carmel, IN (US); Maria Rosario Gonzalez-Garcia, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/748,627

(22) Filed: Jan. 24, 2013

(65) Prior Publication Data
US 2013/0197039 A1 Aug. 1, 2013

Related U.S. Application Data

(60) Provisional application No. 61/592,717, filed on Jan. 31, 2012.

(51) Int. Cl.
C07D 211/72 (2006.01)
A61K 31/44 (2006.01)

(52) U.S. Cl.
USPC .......................... 546/290; 514/345

(58) Field of Classification Search
None
See application file for complete search history.

(56) References Cited

U.S. PATENT DOCUMENTS

2009/0163545 A1* 6/2009 Goldfarb ................ 514/312
2011/0275647 A1  11/2011 Arakawa et al.

FOREIGN PATENT DOCUMENTS

| EP | 1655283 | 5/2006 |
| EP | 1659113 | 5/2006 |
| EP | 2078719 | 9/2007 |
| WO | 2010095767 | 8/2010 |
| WO | 2013/112323 | 8/2013 |
| WO | 2013/116065 | 8/2013 |

OTHER PUBLICATIONS

Yen, et al., "MAT2, a Monoacylglycerol Acyltransferase Expressed in the Small Intestine," The Journal of Biological Chemistry, vol. 278, No. 20, Issue of May 16, pp. 18532-18537 (2003).
Hall, et al., "Evidence for regulated monoacylglycerol acyltransferase expression and activity in human liver," Journal of Lipid Research, vol. 53, pp. 990-999 (2012).
Cao, et al., "A Predominant Role of Acyl-CoA:monoacylglycerol Acyltransferase-2 in Dietary Fat Absorption Implicated by Tissue Distribution, Subcellular Localization, and Up-regulation by High Fat Diet," The Journal of Biological Chemistry, vol. 279, No. 18, Issue of Apr. 30, pp. 18878-18886 (2004).
Yen, et al., "Deficiency of the intestinal enzyme acyl CoA:monoacylglycerol acyltransferase-2 protects mice from metabolic disorders induced by high-fat feeding," Nature Medicine, vol. 15, No. 4, pp. 442-446 (2009).

* cited by examiner

*Primary Examiner* — Janet L Andres
*Assistant Examiner* — Heidi Reese
(74) *Attorney, Agent, or Firm* — James B. Myers

(57) ABSTRACT

The present invention provides compounds of Formula below:

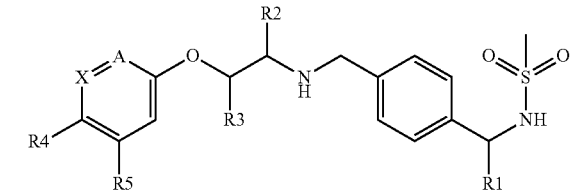

and analogues thereof where the various substituent groups, R1, R2, R3, R4, R5 A, and X are described herein; or a pharmaceutical salt thereof; a method of treating a condition such as hypertriglyceridemia and a process for preparing the compounds.

27 Claims, No Drawings

BENZYL SULFONAMIDE DERIVATIVES USEFUL AS MOGAT-2 INHIBITORS

Ingestion of excess dietary fat is a leading cause of diet induced obesity and can have a profound detrimental effect on a people's health. More than 90% of dietary fat for humans is triacylglycerol (or triglyceride), which is nearly completely absorbed by the small intestine. The enzyme acyl CoA: monoacylglycerol acytransferase-2 (MOGAT-2) is believed to play an important role in the absorption of dietary fat in the small intestines. It has been demonstrated that MOGAT-2 deficient mice when fed a high fat diet are protected against developing obesity, glucose intolerance, hypercholesterolemia and developing a fatty liver. Further, it has also been shown that MOGAT-2 deficient mice exhibit lower plasma triacylglycerol levels after a dietary olive oil challenge. (Yen, et al, *Nat. Med.* 2009, 15(4), 442-446.)

There is a need for additional drugs for the treatments for hypertriglyceridemia. There is also a need to for new inhibitors of the MOGAT-2 receptor. The present invention addresses one or more of these needs by providing alternative compounds and treatment methods, which may be suitable for the treatment hypertriglyceridemia.

The present invention provides a compound according to Formula I:

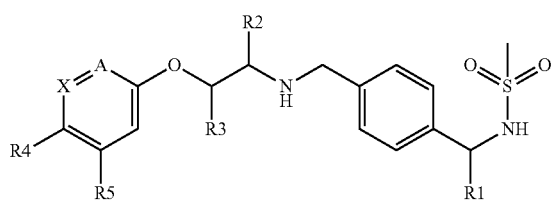

wherein R1 is selected from: —CH$_3$ and —CF$_3$; R2 is selected from: H, —CH$_3$, —CH$_2$OCH$_3$, —CH$_2$OCH$_2$CH$_3$; R3 is selected from: H, —C$_{1-2}$ alkyl, —CH$_2$OCH$_3$, —CH$_2$OCH$_2$CH$_3$; R4 is selected from: H, halogen, and —OCH$_3$; R5 is selected from H and a halogen; A is selected from: CH, CF, CCN, and N; X is selected from: CH, CF, COCH$_3$, and N; provided that only one of X and A is N, or a pharmaceutically acceptable salt thereof.

In one embodiment R1 is —CH$_3$. In another embodiment R1 is —CF$_3$.

Preferably R2 is selected from: H, —CH$_3$, —CH$_2$OCH$_3$. More preferably R2 is selected from: H and —CH$_2$OCH$_3$. Still more preferably R2 is H.

Preferably R3 is selected from: H, —CH$_3$, —CH$_2$OCH$_3$, and —CH$_2$OCH$_2$CH$_3$. More preferably R3 is selected from H, —CH$_2$OCH$_3$, and —CH$_2$OCH$_2$CH$_3$. Still more preferably R3 is —CH$_2$OCH$_3$.

Preferably R4 is selected from: H and F. More preferably R4 is F.

Preferably R5 is H or F. More preferably R5 is H.

Preferably A is selected from CH, CF, and N. More preferably A is selected form CH and N. Still more preferably A is N.

Preferably X is selected from: CH and N. More preferably X is CH.

The present invention provides a compound according to Formula I wherein R1 is —CH$_3$; R2 is selected from: H, —CH$_3$, —CH$_2$OCH$_3$; R3 is selected from H, —CH$_3$, —CH$_2$OCH$_3$ and —CH$_2$OCH$_2$CH$_3$; R4 is selected from: H and F; R5 is selected from: H and F; A is selected from CH, CF, and N; and X is selected from CH and N; provided that only one of X and A is N; or a pharmaceutically acceptable salt thereof.

The present invention provides a compound according to Formula I wherein R1 is —CH$_3$; R2 is selected from: H and —CH$_2$OCH$_3$; R3 is selected from H, —CH$_2$OCH$_3$, and —CH$_2$OCH$_2$CH$_3$; R4 is selected from H and F; R5 is selected from H and F; A is selected from CH and N; and X is selected from CH and N; provided that only one of X and A is N or a pharmaceutically acceptable salt thereof.

The present invention provides a compound according to Formula I wherein R1 is —CH$_3$; R2 is —CH$_3$; R3 is —CH$_2$OCH$_3$; R4 is F; R5 is H; A is N; and X is CH; provided that only one of X and A is N or a pharmaceutically acceptable salt thereof.

The present invention provides a compound according to Formula I wherein R1 is —CF$_3$; R2 is selected from: H, —CH$_3$, —CH$_2$OCH$_3$; R3 is selected from H, —CH$_3$, —CH$_2$OCH$_3$ and —CH$_2$OCH$_2$CH$_3$; R4 is selected from: H and F; R5 is selected from: H or F; A is selected from CH, CF, and N; and X is selected from CH and N; provided that only one of X and A is N; or a pharmaceutically acceptable salt thereof.

The present invention provides a compound according to Formula I wherein R1 is —CF$_3$; R2 is selected from: H and —CH$_2$OCH$_3$; R3 is selected from H, —CH$_2$OCH$_3$, and —CH$_2$OCH$_2$CH$_3$; R4 is selected from H and F; R5 is selected from H and F; A is selected from CH and N; and X is selected from CH and N; provided that only one of X and A is N or a pharmaceutically acceptable salt thereof.

The present invention provides a compound according to Formula I wherein R1 is —CF$_3$; R2 is —CH$_3$; R3 is —CH$_2$OCH$_3$; R4 is selected from: F; R5 is F; A is N; and X is CH; provided that only one of X and A is N, or a pharmaceutically acceptable salt thereof.

The present invention provides a compound according to Formula II
and

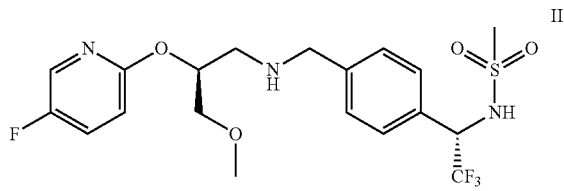 [SMILES: COC[C@H](CNCc1ccc([C@H](NS(C)(=O)=O)C(F)(F)F)cc1)Oc1ccc(F)cn1]

or a pharmaceutically acceptable salt thereof. Preferably the pharmaceutically acceptable salt is a hydrogen chloride addition salt to provide a compound which is N-[(1S)-2,2,2-trifluoro-1-{4-[({(2S)-2-[(5-fluoropyridin-2-yl)oxy]-3-methoxypropyl}amino)methyl]phenyl}ethyl]methanesulfonamide hydrochloride.

The present invention provides a compound which is N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form characterized by an X-ray powder diffraction pattern obtained from a CuKα source (λ=1.54056 Å), which comprises peaks at: a) 14.95°, 18.13°, and 21.14°+/−0.2° in 2θ; or b) 12.71°, 14.95°, 18.13°, 18.67°, 21.14°, and 27.76°+/−0.2° in 2θ; or c) 5.46°, 11.10°, 12.71°, 13.97°, 14.95°, 18.13°, 18.67°, 21.14°, and 27.76°, +/−0.2° in 2θ.

The present invention provides a composition comprising substantially pure N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form. As used herein "substantially pure" refers to a composition with greater than 80% w/w of the crystalline material, more preferably greater than 95% w/w of the crystalline material, and still yet more preferably greater than 98% w/w of the crystalline N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt.

The present invention also provides a pharmaceutical composition comprising a compound according to any one of the compounds of Formula I or II, or a pharmaceutically acceptable salt thereof, and a pharmaceutically acceptable carrier, diluent, or excipient.

The present invention also provides a method of treating a patient in need of treatment for hypertriglyceridemia. The method comprises administering to the patient an effective amount of a pharmaceutical composition comprising a compound according to Formula I or II, or a pharmaceutically acceptable salt thereof.

The present invention also provides a method of treating a patient in need of treatment for hypertriglyceridemia, the method comprises administering to the patient an effective amount of a compound according to Formula I or II, or a pharmaceutically acceptable salt thereof.

As used herein patient refers to an animal in need of treatment, preferably not exclusively a mammal, preferably a human; or alternatively a companion animal, such as a dog or cat; or a fowl.

The present invention also provides a compound according to Formula I or II, or a pharmaceutically acceptable salt thereof, for use in therapy.

The present invention also provides a compound according to Formula I or II, or a pharmaceutically acceptable salt thereof, for use in the treatment of hypertriglyceridemia.

The present invention also provides for the use a compound according to Formula I or II, or a pharmaceutically acceptable salt thereof, in the manufacture of a medicament to treat hypertriglyceridemia.

The term "pharmaceutically-acceptable salt" as used herein refers a salt of a compound according to Formula I or II considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

GENERAL CHEMISTRY

As used herein, the following terms have the meanings indicated: "DCM" refers to dichloromethane; "DEA" refers to diethylamine; "Et$_2$O" refers to diethylether; "DMEA" refers to dimethylethylamine; "DMF" refers to dimethylformamide; "DMSO" refers to dimethylsulfoxide; "de" refers to diastereomeric excess; "ee" refers to enantiomeric excess; "EtOAc" refers to ethyl acetate; "EtOH" refers to ethanol; "IPA" refers to isopropyl alcohol; "HPLC" refers to High Performance Liquid Chromatography; "Isomer 1" refers to the first isomer eluting from a chromatography column; "Isomer 2" refers to the second isomer eluting from a chromatography column; "LC/MS" refers to liquid chromatography followed by mass spectroscopy; "MeOH" refers to methanol; "mesyl" refers to salt or ester of methylsulfonic acid; "MS" refers to mass spectroscopy; "NMR" refers to nuclear magnetic resonance; "OMs" refers to methylsulfonyl ester; "OTs" refers to an 4-toluenesulfonic ester; "SFC" refers to supercritical fluid chromatography; "TLC" refers to thin layer chromatography; "THF" refers to tetrahydrofuran; "tosyl" refers to salt of ester of 4-toluenesulfonic acid.

Unless noted to the contrary, the compounds illustrated herein are named and numbered using either ACDLABS or Symyx Draw 3.2.

Scheme 1 illustrates a general synthesis of compound of Formula I.

Scheme 1

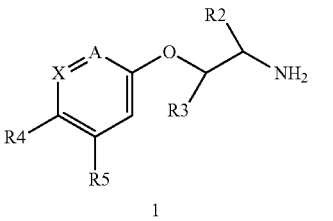

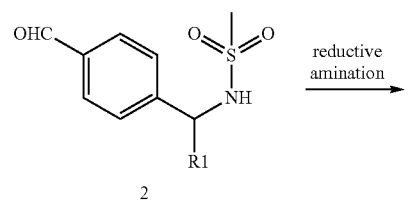

reductive amination →

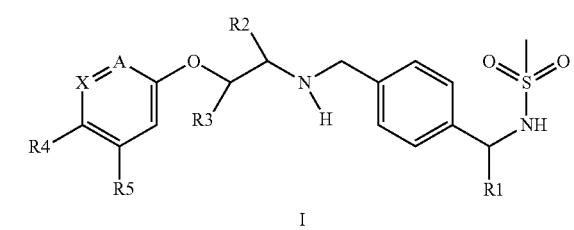

I

Substituted amine 1, which is either commercially available or synthesized by known literature methods, reacts with aldehyde 2 under reductive amination conditions known to skilled artisans to provide compounds of Formula I. For representative examples reductive amination conditions see: Richard C. Larock, *Comprehensive Organic Transformations: a guide to functional group preparations*, 2$^{nd}$ edition, Page 835-846, Wiley-VCH, (1999). More specifically, amine 1 reacts with aldehyde 2 with the presence of a reducing agent, such as triacetoxyborohydride, and an acid, such as acetic acid, in a solvent, such as dichloromethane, to provide the compounds of Formula I, which can be converted to a suitable salt by the addition of an acid, such as hydrochloric acid or maleic acid.

Scheme 2 illustrates an alternative synthesis of compounds of Formula I.

Scheme 2

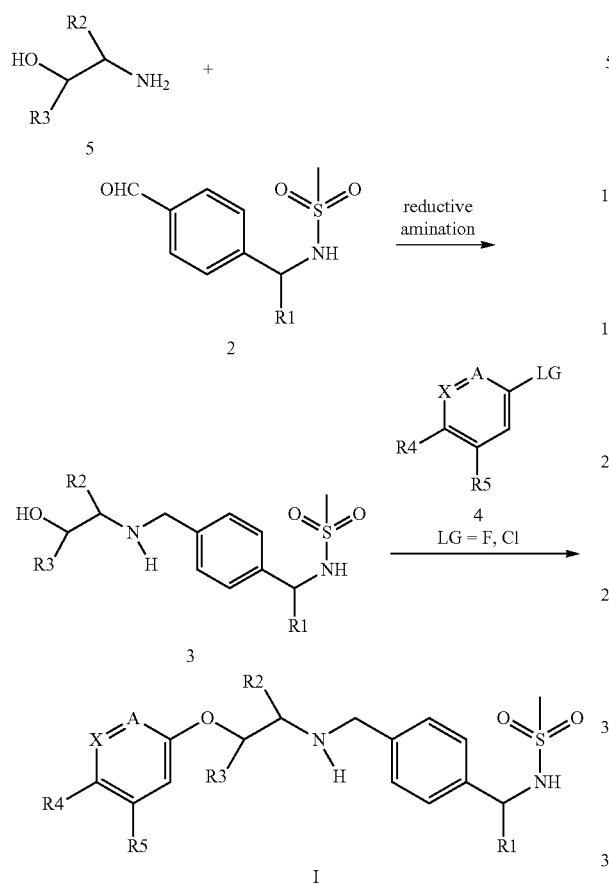

A suitably substituted amino alcohol 5, which is either commercially available or synthesized by known literature methods, reacts with aldehyde 2 under reductive amination conditions as described above to provide compound 3. Compound 3 is combined with a substituted (hetero)aryl 4, which has a leaving group (LG), under elevated temperature and a base, such as sodium hydride, in a solvent, such as dioxane, to provide the compounds of Formula I. Examples of leaving groups (LG) include halogens such as F or Cl. The compounds of Formula I can be further converted to a pharmaceutically acceptable salt with the addition of an acid, such as hydrochloric acid, maleic acid, phosphoric acid, and the like.

Scheme 3 illustrates a synthesis of the intermediate compounds for use in the this invention.

Scheme 3

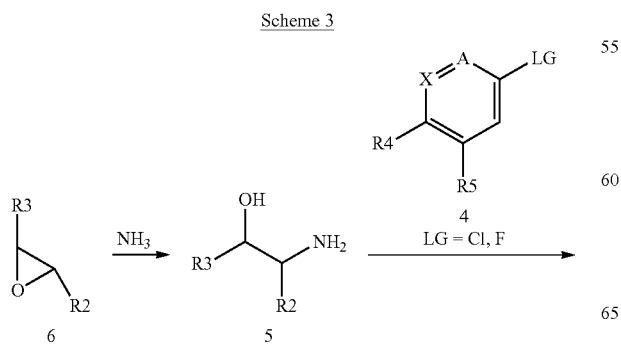

A substituted oxirane 6 reacts with ammonia in a solvent, such as methanol, to provide the amino alcohol 5. Amino alcohol 5 further reacts usually at an elevated temperature with (hetero)aryl 4, which has a leaving group (LG) such as fluorine or chlorine, in the presence of a base such as sodium hydride, in a solvent such as dioxane, to provide the intermediate compounds 1.

Preparation 1

(N—Z)—N-[(4-Bromophenyl)methylene]-(R)-2-methyl-propane-2-sulfinamide

Add (R)-2-methylpropane-2-sulfinamide (40.5 g, 0.33 mol) portionwise to a solution of 4-bromobenzaldehyde (65.57 g, 0.35 mol) in toluene (283 mL). Stir the mixture at ambient temperature for 15 minutes and then add sodium hydroxide (1.34 g, 0.33 mol). Stir the suspension at ambient temperature for 12 hours. Add sodium sulphate (16 g) and Celite® (16 g) and stir the suspension for 15 minutes. Filter and concentrate the filtrate under reduced pressure. Purify the residue by silica gel chromatography eluting with hexane/EtOAc (100% to 70% hexane) to afford the title compound as a white solid (85.5 g, 88% yield). MS (m/z): 288 (M+1).

Preparation 2

N-[(1S)-1-(4-Bromophenyl)-2,2,2-trifluoro-ethyl]-(R)-2-methyl-propane-2-sulfinamide Add neat (trifluoromethyl)trimethylsilane (109 mL, 0.74 mol) at 0° C. to a stirred solution of tetrabutylammonium acetate (88 g, 0.29 mol) and (N—Z)—N-[(4-bromophenyl)methylene]-(R)-2-methyl-propane-2-sulfinamide (85 g, 0.29 mol) in DMF (1.2 L) at 0° C. Stir the mixture at 0-5° C. for 90 minutes. Add saturated aqueous ammonium chloride solution (1.2 L) and extract with EtOAc (4×400 mL). Combine the organic extracts and sequentially wash with water then brine (2×1 L); dry over magnesium sulphate; filter; and concentrate the filtrate under reduced pressure. Triturate the residue with hexane (200 mL) for 10 minutes; filter; and dry the filtrate under vacuum to afford the title compound as a yellow solid (81 g, 76% yield, >98 de). MS (m/z): 358 (M+1).

Preparation 3

(1S)-1-(4-Bromophenyl)-2,2,2-trifluoroethanamine

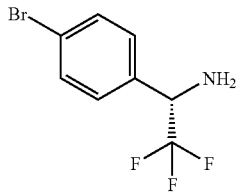 [SMILES: N[C@@H](c1ccc(Br)cc1)C(F)(F)F]

Add HCl (4M in dioxane, 226 mL, 0.9 mol) to a suspension of N-[(1S)-1-(4-bromophenyl)-2,2,2-trifluoro-ethyl]-(R)-2-methyl-propane-2-sulfinamide (81 g, 0.23 mol) in MeOH (670 mL). Stir the mixture at ambient temperature for one hour. Remove the solvent under reduced pressure and triturate the residue with methyl tert-butyl ether (200 mL) for 10 minutes to give the HCl salt as a brown solid. Dissolve the salt in water (1.2) and add 2N NaOH solution raise the pH to 10. Extract the mixture with methyl tert-butyl ether (3×500 mL). Wash the organic phase with water then brine (500 mL each); dry over magnesium sulphate; filter; and concentrate the filtrate under vacuum to give the title compound as a yellow solid (46 g, 80% yield, 98% ee). MS (m/z): 358 (M+1).

Preparation 4

N-[(1S)-1-(4-Bromophenyl)-2,2,2-trifluoro-ethyl]methanesulfonamide

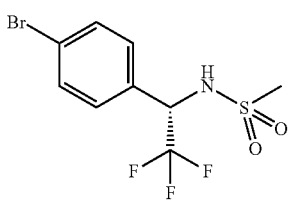 [SMILES: CS(=O)(=O)N[C@@H](c1ccc(Br)cc1)C(F)(F)F]

Add methanesulfonyl chloride (16.42 mL, 0.21 mol) dropwise to a mixture of (1S)-1-(4-bromophenyl)-2,2,2-trifluoroethanamine (49 g, 0.19 mol), 4-dimethylaminopyridine (1.18 g, 9.0 mmol), 2,6-lutidine (67 mL, 0.57 mol) in DCM (250 mL) at 0° C. Warm the mixture to ambient temperature and stir at that temperature for 20 hours. Dilute the reaction mixture with DCM (300 mL) and wash it sequentially with 2M HCl (2×200 mL), water (250 mL), then brine (250 mL). Collect the organic phase and dry over magnesium sulphate; filter; and concentrate the filtrate under reduced pressure. Triturate the residue with hexane (200 mL) for 10 minutes; filter; and dry the solid under reduced pressure to provide the title compound as a pale brown solid (60 g, 93% yield, 98% ee). MS (m/z): 332 (M+1).

Preparation 5

N-[(1S)-2,2,2-Trifluoro-1-(4-formylphenyl)ethyl]methanesulfonamide

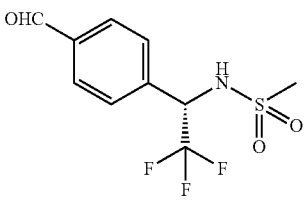 [SMILES: CS(=O)(=O)N[C@@H](c1ccc(C=O)cc1)C(F)(F)F]

Charge a 2 L PARR reactor, with: N-[(1S)-1-(4-bromophenyl)-2,2,2-trifluoro-ethyl]methanesulfonamide (30 g, 90 mmol), palladium(II) acetate (0.81 g, 3.6 mmol), butyldi-1-adamantylphosphine (3.89 g, 10.84 mmol), and tetramethylethylenediamine (10.50 g, 90 mmol) in toluene (1.5 mL). Seal the reactor and pressurize the reactor with synthesis gas (1:1 $CO/H_2$) to 75 psi. Stir the reaction mixture at 95° C. for 16 hours. Cool the mixture; vent; and open the reactor. Filter the mixture through Celite® and concentrate the filtrate under reduced pressure. Purify the crude residue by silica gel chromatography eluting with hexane/EtOAc (8:2 to 1:1) to afford the title compound (22.8 g, 90%, 80% ee). Enrich the chiral purity by using a chiral column: Chiralpak AS-H (2.1×25 cm, 5 μM) $CO_2$/EtOH (9:1) to get the title compound (19 g, 75% yield, 98% ee). MS (m/z): 282 (M+1).

Preparation 6

N-[(1R)-1-(4-Bromophenyl)ethyl]methanesulfonamide

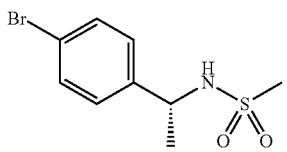

Add methanesulfonyl chloride (13.44 mL, 0.17 mmol) to a mixture of (1R)-1-(4-bromophenyl)ethanamine (25 g, 0.12 mol) and triethylamine (51 mL, 0.36 mol) in DCM (250 mL) at 0° C. Warm mixture to ambient temperature and stir for 2.5 hours. Wash the reaction mixture with 2M aqueous HCl (100 ml). Separate the organic phase and water phase. Sequentially wash the organic phase with water then brine (2×100 mL). Dry the organic phase over anhydrous sodium sulphate; filter; and concentrate the filtrate under reduced pressure to provide a residue. Triturate the residue with hexane (150 mL), filter and dry under reduced pressure to afford the title compound as a yellow solid (33.24 g, 96%, ee>98%). MS (m/z): 278 (M+1).

Preparation 7

N-[(1R)-1-(4-Formylphenyl)ethyl]methanesulfonamide

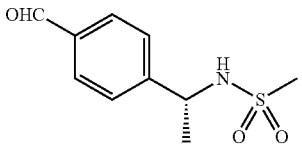

Charge a 300 mL PARR reactor with N-[(1R)-1-(4-bromophenyl)ethyl]-methanesulfonamide (10 g, 35 mmol), (1,1'-bis(diphenylphosphino)-ferrocene)palladium(II) chloride (733 mg, 0.9 mmol), sodium carbonate (3.81 g, 35 mmol) and DMF (50 mL). Add triethylsilane (11.6 mL, 0.72 mmol) and purge the reactor with carbon monoxide three times. Pressurize the PARR reactor with carbon monoxide (50 psi) and stir the mixture at 90° C. for 15 hours. Cool the reactor to ambient temperature; filter through Celite® pad; and wash the pad with DCM (150 mL). Sequentially wash the filtrate with water then brine (2×80 mL). Concentrate the organic phase under reduced pressure to provide an orange oil residue. Purify the residue by silica gel flash chromatography eluting with hexane/EtOAc (0 to 30% EtAc) to provide the title compound (5.6 g, 70%, ee>98%). MS (m/z): 228 (M+1).

Preparation 8

(2S)-1-Amino-3-methoxy-2-propanol

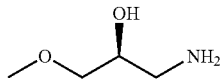

Add S-methyl glycidyl ether (25 mL, 278.7 mmol) to a solution of ammonia in MeOH (7M, 796 mL, 5.6 mol) and stir for 14 hours at ambient temperature. Concentrate under reduced pressure at 20° C. to give the title compound as a colorless oil (31.0 g). $^1$H NMR (300 MHz, CDCl$_3$): δ 3.86-3.81 (m, 1H), 3.38-3.33 (m, 5H), 2.81-2.64 (m, 2H), 2.17 (s, 4H).

The following compounds in Table 1 are prepared essentially by the method of Preparation 8.

TABLE 1

| Prep | Chemical Name | Structure | Physical data MS (m/z): |
|---|---|---|---|
| 9 | 1-Amino-3-ethoxy-propan-2-ol | 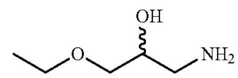 | 120 (M + 1) |
| 10 | (2R)-1-Amino-3-ethoxy-propan-2-ol | 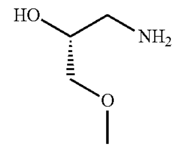 | 106 (M + 1) |

Preparation 11

(2S)-2-[(5-Fluoropyridin-2-yl)oxy]-3-methoxypropan-1-amine

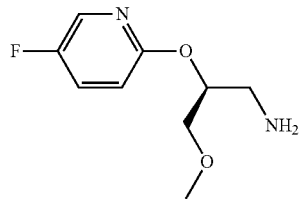

Suspend sodium hydride (60% in mineral oil, 13.56 g, 339.1 mmol) in dimethylacetamide (245.7 mL) and add a solution of (2S)-1-amino-3-methoxy-2-propanol (31.0 g, 147.4 mmol) in dimethylacetamide (59.0 mL) over 30 minutes. Stir for one hour; then add 2,5-difluoropyridine (17.03 mL, 162.17 mmol) over a 30 min interval; and stir at ambient temperature for an additional 1.5 hours. Slowly add water (930 mL) to quench the reaction. Extract the resulting mixture with EtOAc (4×300 mL) and combine the organic extracts. Dry the combined extracts over magnesium sulfate; filter and concentrate the filtrate under reduced pressure. Purify via flash column chromatography using a gradient of 0 to 10% EtOAc in DCM to give the title compound as a brown oil (12.0 g). MS (m/z): 201 (M+1).

The following compounds in Table 2 are prepared essentially by the method of Preparation 11.

TABLE 2

| Prep # | Chemical name | Structure | Physical data MS (m/z): |
|---|---|---|---|
| 12 | (2R)-2-(2-Pyridyloxy)propan-1-amine | 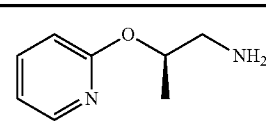 | 153 (M + 1) |

TABLE 2-continued

| Prep # | Chemical name | Structure | Physical data MS (m/z): |
|---|---|---|---|
| 13 | (2S)-3-Methoxy-2-(2-pyridyloxy)propan-1-amine | 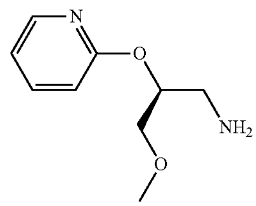 | 183 (M + 1) |
| 14 | (2R)-2-[(5-Fluoro-2-pyridyl)oxy]-3-methoxy-propan-1-amine | 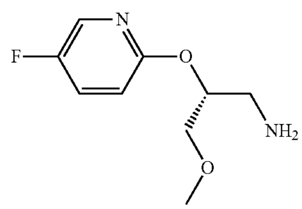 | 201 (M + 1) |
| 15 | (2R)-2-(3-Pyridyloxy)propan-1-amine | 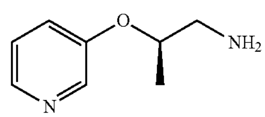 | 153 (M + 1) |
| 16 | 2-[(5-Fluoropyridin-2-yl)oxy]ethanamine | 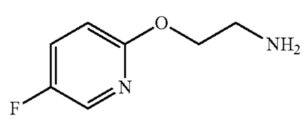 [SMILES: NCCOc1ccc(F)cn1] | 157 (M + 1) |
| 17 | (2S)-2-[(5-Fluoro-3-pyridyl)oxy]-3-methoxy-propan-1-amine | 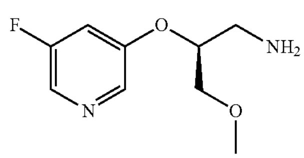 | 201 (M + 1) |
| 18 | 3-Ethoxy-N,N-bis[(4-methoxyphenyl)methyl]-2-(2-pyridyloxy)propan-1-amine | 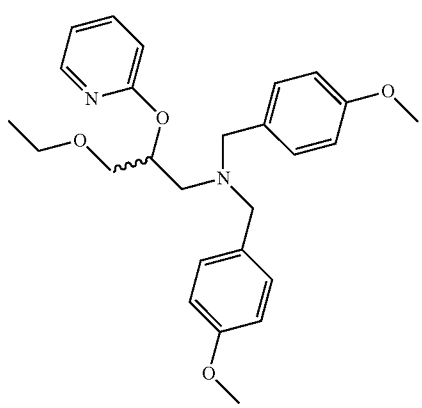 [SMILES: CCOCC(CN(Cc1ccc(OC)cc1)Cc1ccc(OC)cc1)Oc1ccccn1] | 437 (M + 1) |

TABLE 2-continued

| Prep # | Chemical name | Structure | Physical data MS (m/z): |
|---|---|---|---|
| 19 | 3-Ethoxy-2-[(5-fluoro-2-pyridyl)oxy]-N,N-bis[(4-methoxyphenyl)methyl]propan-1-amine | 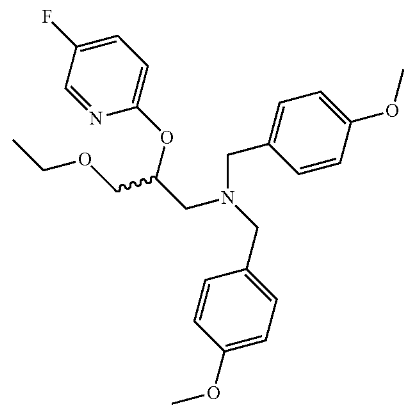 [SMILES: CCOCC(CN(Cc1ccc(OC)cc1)Cc1ccc(OC)cc1)Oc1ccc(F)cn1] | 455 (M + 1) |
| 20 | 3-(4-Fluorophenoxy)-2-methoxy-propan-1-amine | 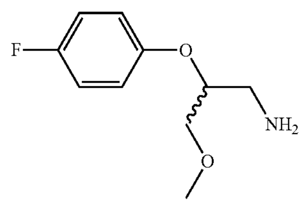 | 200 (M + 1) |
| 21 | (2S)-1-[(5-Fluoro-2-pyridyl)oxy]propan-2-amine | 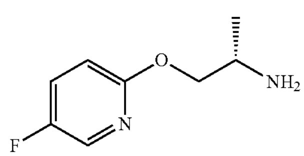 | 171 (M + 1) |
| 22 | 2-(2-Pyridyloxy)butan-1-amine | 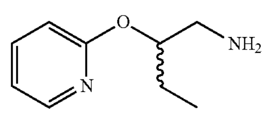 | 167 (M + 1) |
| 23 | 2-(4-Fluoropyridin-2-yloxy)ethanamine | 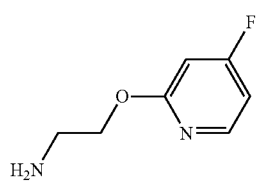 [SMILES: NCCOc1cc(F)ccn1] | 157 (M + 1) |

Preparation 24

2-[(4-Fluorophenoxy)methyl]oxirane

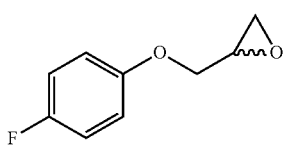 [SMILES: Fc1ccc(OCC2CO2)cc1]

Dissolve 4-fluorophenol (5 g, 43.3 mmol) in DMSO (18.8 mL) and add potassium hydroxide (14.28 g, 216.32 mmol) followed by chloromethyloxirane (61.06 mL, 264.8 mmol). Stir at ambient temperature, monitoring the reaction by TLC (50% DCM/hexanes) until complete. Pour the mixture into water and extract with EtOAc. Wash the organic extracts with saturated aqueous NH₄Cl solution and then brine. Dry over Na₂SO₄; filter; and concentrate the filtrate under reduced pressure. Purify using flash column chromatography on silica gel with a 10% solution of EtOAc in hexanes to elute. Re-purify the obtained product by flash column chromatography with 50% DCM/hexanes to provide the product as a clear oil (3.62 g, 49.8%).

¹H NMR (300 MHz, CDCl₃) δ 6.96-6.92 (m, 2H), 6.85-6.81 (m, 2H), 4.16 (dd, J=3.1, 11.0 Hz, 1H), 3.88 (dd, J=5.7, 11.0 Hz, 1H), 3.32-3.30 (m, 1H), 2.87 (t, J=4.5 Hz, 1H), 2.71 (dd, J=2.6, 4.9 Hz, 1H).

Preparation 25

1-(4-Fluorophenoxy)-3-methoxy-propan-2-ol

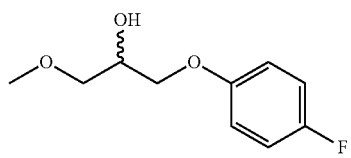

Dissolve 2-[(4-fluorophenoxy)methyl]oxirane (3.62 g, 21.5 mmol) in MeOH (71.7 mL) and add potassium monopersulfate (15.88 g, 25.83 mmol) followed by molybdenum dichloride dioxide (60 mg, 0.32 g). Heat the mixture to reflux while stirring under air for 3 hours, then cool to ambient temperature and stir the mixture overnight. Add additional an amount of potassium monopersulfate (15.88 g, 25.8 mmol) and reflux the resulting mixture for 3 hours. Filter the mixture and wash the filter cake with MeOH. Concentrate the collected filtrate under reduced pressure and then dissolve the resulting material in DCM. Wash the DCM mixture with water and then brine; then dry over Na₂SO₄; filter and concentrate the filtrate under reduced pressure. Purify via flash column chromatography using 20% EtOAc in hexanes to provide the title product as a clear oil (2.73 g, 63.4%). MS (m/z): 218 (M+NH₄).

Preparation 26

1-(4-Fluorophenoxy)-3-methoxy-propan-2-one

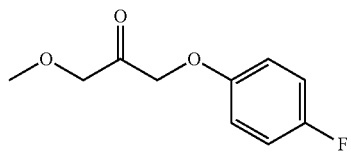

Dissolve 1-(4-fluorophenoxy)-3-methoxy-propan-2-ol (2.6 g, 12.99 mmol) in DCM (26 mL) and add molecular sieves, pyridinium chlorochromate (7.14 g, 32.47 mmol), and pyridine (5.25 mL, 64.93 mmol). Stir the mixture at ambient temperature overnight. Filter the mixture through a Celite® plug and wash the plug with Et₂O. Concentrate the filtrate; then purify via flash column chromatography using 25% EtOAc in hexanes to provide the product as a clear oil (872 mg, 33.9%). MS (m/z): 216 (M+NH₄).

Preparation 27

1-(4-Fluorophenoxy)-3-methoxy-propan-2-amine

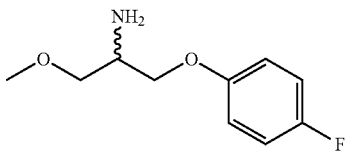

Dissolve 1-(4-fluorophenoxy)-3-methoxy-propan-2-one (860 mg) in ammonia (7N in MeOH, 14.5 mL) and add molecular sieves (1 g). Stir the mixture at ambient temperature overnight. Cool the reaction to 0° C.; add sodium tetrahydroborate (0.66 g, 17.36 mmol); and stir the mixture at ambient temperature for 2 hours. Filter the mixture through a Celite® plug and rinse with MeOH. Concentrate the collected filtrate; dissolve in DCM; and wash with saturated aqueous NaHCO₃ solution. Concentrate the filtrate under reduced pressure. Purify the mixture via SCX column, eluting with 7N NH₃/MeOH to give the title compound (680 mg, 78.6%). MS (m/z): 200 (M+1).

Preparation 28

Diethyl 2-(4-fluorophenoxy)propanedioate

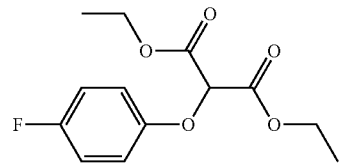 [SMILES: CCOC(=O)C(Oc1ccc(F)cc1)C(=O)OCC]

Dissolve diethyl 2-bromopropanedioate (2.5 g, 10.5 mmol) in DMF (80 mL) and add 14-fluorophenol (12 g, 10 mmol) and K₂CO₃ (1.38 g, 9.99 mmol). Stir the mixture at ambient temperature for 5 hours. Add EtOAc (200 mL) and wash with 3×50 mL H₂O. Dry the organic phase over Na₂SO₄. Filter and concentrate under reduced pressure. Purify via prep-HPLC (PRC-ODS column/20×250 mm, 15 μM; eluting with a gradient of 35-50% water (10 mmol/L NH₄HCO₃) in acetonitrile, collection at 214 nm) to give a residue. Concentrate the residue under reduced pressure to give the title compound as a colorless oil (920 mg, 34.1%). MS (m/z): 271 (M+1).

Preparation 29

2-(4-Fluorophenoxy)propane-1,3-diol

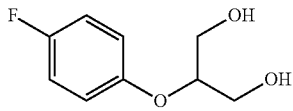

Dissolve diethyl 2-(4-fluorophenoxy)propanedioate (360 mg, 1.33 mmol) in THF (10 mL); slowly add lithium aluminum hydride (1.0 M in THF; 3.6 mL, 3.6 mmol); and stir at ambient temperature for 30 minutes. Quench reaction via the addition of H$_2$O (1 mL) and extract with EtOAc. Dry the organic phase over Na$_2$SO$_4$. Filter and concentrate the filtrate under reduced pressure. Purify the resulting material via silica gel flash column chromatography (12 g), using a gradient of 10%-50% of EtOAc in petroleum ether. Concentrate the desired fractions under reduced pressure to give the title compound as a colorless oil (195 mg, 78.6%). $^1$H NMR (300 MHz, CDCl$_3$) δ 7.0 (m, 4H), 4.3 (m, 1H), 3.9 (m, 4H), 2.4 (bs, 2H).

Preparation 30

2-(4-Fluorophenoxy)-3-methoxy-propan-1-ol

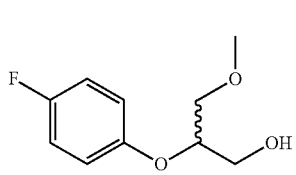

Dissolve 2-(4-fluorophenoxy)propane-1,3-diol (186 mg, 0.99 mmol) in THF (5 mL), and add sodium hydride (60% dispersion in mineral oil, 24 mg, 1 mmol). Stir the mixture for 30 minutes at ambient temperature then add iodomethane (0.4 mL, 4.09 mmol). Stir the reaction at ambient temperature for 16 hours. Remove the solvents under reduced pressure and add water to the residue. Extract with EtOAc three times; collect the EtOAc extracts; dry; and remove the solvents under reduced pressure. Purify the residue via prep-TLC using 1:1 EtOAc:petroleum ether, to give the title compound (50 mg, 31.0%). $^1$H NMR (300 MHz, CDCl$_3$) δ 7.0 (m, 4H), 4.2-4.5 (m, 2H), 3.8 (m, 2H), 3.55 (m, 1H), 3.35 (m, 2H), 2.35 (bs, 1H), 2.0 (s, 3H).

Preparation 31

1-Ethoxy-3-(4-fluorophenoxy)propan-2-ol

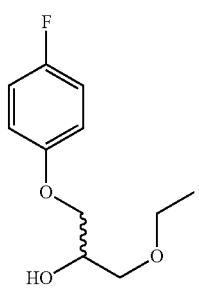

Slowly add sodium (1 g, 43.5 mmol) to absolute EtOH (80 mL) and stir the mixture at ambient temperature for 2 hours. Add 2-[(4-fluorophenoxy)methyl]oxirane (2.0 g, 11.89 mmol) in a single portion and stir for 16 hours at ambient temperature. Add 30 mL EtOAc; wash with H$_2$O (10 mL) three times; then dry the organic layer over Na$_2$SO$_4$; filter; and concentrate the filtrate under reduced pressure to give the title compound (2.55 g, 86.3%) as a yellow oil. $^1$H NMR (300 MHz, d$_6$-DMSO) δ 7.15 (m, 2H), 6.95 (m, 2H), 5.05 (m, 1H), 3.95 (m, 3H), 3.49 (m, 4H), 1.05 (t, 3H).

Preparation 32

[1-(Ethoxymethyl)-2-(4-fluorophenoxy)ethyl]methanesulfonate

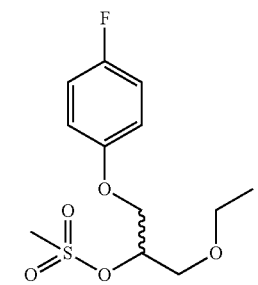 [SMILES: CCOCC(COc1ccc(F)cc1)OS(C)(=O)=O]

Charge a reaction vessel with 1-ethoxy-3-(4-fluorophenoxy)propan-2-ol (2.2 g, 10.27 mmol), triethylamine (110 mg, 1.09 mmol), DCM (30 mL) and methanesulfonyl chloride (1.18 g, 10.27 mmol). Stir for 16 hours at ambient temperature. Remove the solvent under reduced pressure. Add 100 mL EtOAc, wash the organic layer with H$_2$O (20 mL×3); dry over Na$_2$SO$_4$; filter; and concentrate the filtrate under reduced pressure to provide the title compound as a brown oil (2.30 g, 76.6%). $^1$H NMR (300 MHz, CD$_3$OD) δ 7.0 (m, 2H), 6.95 (m, 2H), 5.0 (m, 1H), 4.18 (d, 2H), 3.80 (d, 2H), 3.60 (m, 2H), 3.10 (s, 3H), 1.10 (t, 3H).

Preparation 33

[2-(4-Fluorophenoxy)-3-methoxy-propyl]methanesulfonate

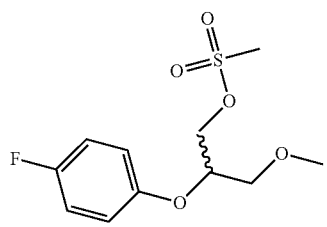 [SMILES: COCC(COS(C)(=O)=O)Oc1ccc(F)cc1]

Prepare [2-(4-fluorophenoxy)-3-methoxy-propyl]methanesulfonate essentially by the method of Preparation 32. GC-MS (m/z) 278 (M+).

Preparation 34

1-Ethoxy-3-(4-fluorophenoxy)propan-2-amine

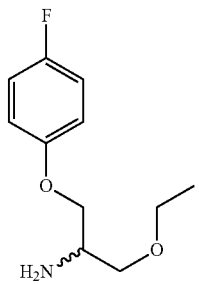

Dissolve [1-(ethoxymethyl)-2-(4-fluorophenoxy)ethyl] methanesulfonate (2.3 g, 7.87 mmol) in DMF (3 mL) and add sodium azide (1 g, 15.38 mmol) to the mixture. Stir the mixture at 70° C. for 3 hours. Add Et$_2$O (150 mL) and wash with water (3×10 mL). Separate the phases; dry the organic phase over Na$_2$SO$_4$; filter; and concentrate the filtrate under reduced pressure to give a clear oil. Dissolve the oil in a mixture of THF (50 mL) and H$_2$O (12.5 mL). Add triphenylphosphine (3.0 g, 11.44 mmol) and stir at 30° C. for 2 hours. Purify the reaction mixture via SCX-ion exchange chromatography with 1N NH$_3$/MeOH to provide the product fractions. Concentrate the select fractions under reduced pressure and then purify via flash column chromatography using a gradient of 1% to 10% of MeOH in DCM collecting fractions at wavelength of 214 nm. Concentrate under reduced pressure to give the title compound as a colorless oil (880 mg, 33.5%). MS (m/z): 214 (M+1).

Preparation 35

1-(4-Fluorophenoxy)-3-methoxy-propan-2-amine

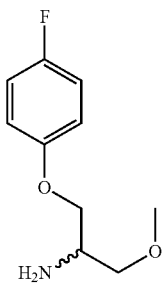

Prepare 1-(4-Fluorophenoxy)-3-methoxy-propan-2-amine essentially by the method of Preparation 34. MS (m/z) 200 (M+1).

Preparation 36

3-Ethoxy-2-(2-pyridyloxy)propan-1-amine

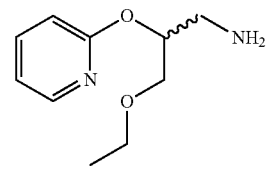

Combine 3-ethoxy-N,N-bis[(4-methoxyphenyl)methyl]-2-(2-pyridyloxy)propan-1-amine (1.05 g, 2.41 mmol), palladium/carbon (5%, 0.11 g, 0.05 mmol), and tert-butyl alcohol (15 mL). Purge with hydrogen gas 3 times and then stir the mixture at 50° C. under an atmosphere of hydrogen gas for 4 days. Filter the reaction through a Celite® plug and rinse the plug with EtOAc (2×30 mL). Collect the filtrate and concentrate under reduced pressure to afford the title compound (0.42 g, 89.0%) as a yellow oil. MS (m/z): 197 (M+1).

Preparation 37

3-Ethoxy-2-[(5-fluoro-2-pyridyl)oxy]propan-1-amine

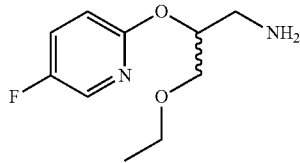

Prepare 3-ethoxy-2-[(5-fluoro-2-pyridyl)oxy]propan-1-amine essentially by the method of Preparation 36.

Preparation 38

N-[(1S)-2,2,2-Trifluoro-1-[4-[[[(2R)-2-hydroxypropyl]amino]methyl]phenyl]ethyl]methanesulfonamide

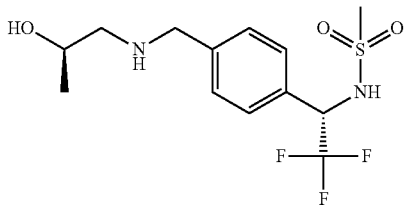 [SMILES: C[C@@H](O)CNCc1ccc([C@H](NS(C)(=O)=O)C(F)(F)F)cc1]

Dissolve (2R)-1-aminopropan-2-ol (0.4 g, 5.33 mmol) in DCM (10.6 mL); then acetic acid (366.2 uL, 6.39 mmol) and N-[(1S)-2,2,2-trifluoro-1-(4-formylphenyl)-ethyl]-methanesulfonamide (1.65 g, 5.86 mmol). Stir the resulting mixture at ambient temperature for 2 hours; then add sodium triacetoxyborohydride (2.82 g, 13.31 mmol); and stir at ambient temperature overnight. Add MeOH (1 mL) and evaporate a portion of the solvent under reduced pressure. Purify via SCX chromatography eluting with 2M $NH_3$/MeOH. Concentrate the appropriate fractions under reduced pressure to give the title compound (1.7 g, 93.8%). MS (m/z): 341 (M+1).

Preparation 39

N-[(1R)-1-[4-[[[(2R)-2-Hydroxypropyl]amino]methyl]phenyl]ethyl]methanesulfonamide

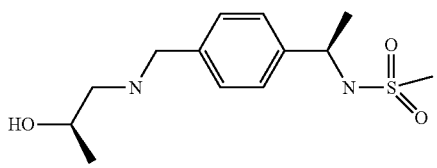 [SMILES: C[C@@H](O)CNCc1ccc([C@@H](C)NS(C)(=O)=O)cc1]

Prepare N-[(1R)-1-[4-[[[(2R)-2-Hydroxypropyl]amino] methyl]phenyl]ethyl]methanesulfonamide essentially by the method of Preparation 38. MS (m/z) 287 (M+1).

EXAMPLE 1

N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide hydrochloride

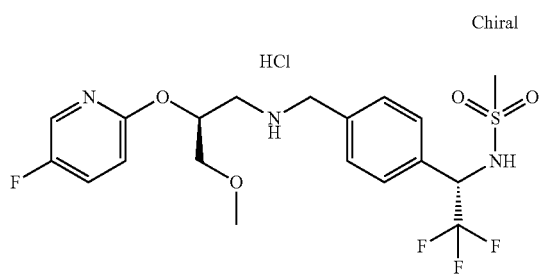 [SMILES: Cl ; COC[C@H](CNCc1ccc([C@H](NS(C)(=O)=O)C(F)(F)F)cc1)Oc1ccc(F)cn1]

Method 1:

Dissolve (2S)-2-[(5-fluoropyridin-2-yl)oxy]-3-methoxypropan-1-amine (25.0 g, 124.9 mmol) in MeOH (416.2 mL) and add N-[(1S)-2,2,2-trifluoro-1-(4-formylphenyl)ethyl] methanesulfonamide (35.12 g, 124.87 mmol) portionwise. Stir the mixture for 2 hours; cool it to 0° C.; then add sodium tetrahydroborate (14.17 g, 374.6 mmol) portionwise over 50 minutes controlling the rate of addition to keep the temperature below ambient temperature. Stir the mixture for 1.5 hours at ambient temperature; then cool it to 0° C.; and slowly add water (90 mL) to quench the reaction. Allow the mixture to warm to ambient temperature and concentrate under reduced pressure. Dilute with water (50 mL) and extract with EtOAc (2×200 mL). Combine the EtOAc extracts; dry over $MgSO_4$; filter; and concentrate the filtrate under reduced pressure. Purify the crude material using a silica gel flash column chromatography eluting with a gradient of 50-80% EtOAc/ DCM to give an oil (46.5 g, 78%). MS (m/z): 466 (M+1).

Dissolve the oil (46 g, 98.8 mmol) in DCM (276 mL). Add hydrogen chloride (5M in $Et_2O$; 494.1 mL, 494.1 mmol). Triturate with a spatula; then concentrate under vacuum; and dry in a vacuum oven at 45° C. overnight, then at 50° C. for 24 hours to give the title compound as a white solid (48.0 g, 90.2%). MS (m/z): 466 (M+1-Cl).

Method 2:

Dissolve (2S)-2-[(5-fluoropyridin-2-yl)oxy]-3-methoxypropan-1-amine (100.0 g, 0.5 mol) in THF (1.6 L) and add N-[(1S)-2,2,2-trifluoro-1-(4-formylphenyl)-ethyl]-methanesulfonamide (140 g, 0.5 mol) portionwise keeping temperature constant via an ambient temperature water bath. Stir the mixture for 2.5 hours. Cool to 15° C. and add sodium triacetoxyborohydride (211 g, 1 mol) portion-wise while controlling the rate of addition to keep the temperature below ambient temperature. Stir the mixture for 2 h at ambient temperature. Dilute with EtOAc (500 mL) and pour into a 0° C. solution of sodium bicarbonate (209 g) in 1 L of water. Separate the layers; dry the organic layer over $MgSO_4$; filter; and concentrate the filtrate under reduced pressure. Purify using flash column chromatography with DCM/EtOAC with a gradient of 8:2 to 2:8 to give a thick oil (175 g, 75% yield). MS (m/z): 466 (M+1)

Dissolve 175 g (0.34 mol) of the oil in EtOH (470 mL) and heptane (690 mL) and cool to 10° C. Add hydrogen chloride (4M in dioxane; 1.25 eq, 0.42 mol, 105 mL). Allow to reach ambient temperature and stir for 2 h. Collect the solid by filtration and dry in a vacuum oven at 60° C. overnight to give the title compound as a white solid (150 g, 89%). MS (m/z): 466 (M-Cl)

The following compounds in Table 3 are prepared essentially by method 1 of Example 1. All the following Examples in Table 3 were isolated as single isomers either starting from chiral starting materials and/or using the chromatographic columns and conditions identified below. The separation can be performed with the free base or with its salt form.

TABLE 3

| Ex # | Chemical name | Structure | Physical data MS (m/z): | Chrom. Cond. |
|---|---|---|---|---|
| 2 | N-{(1R)-1-[4-({[(2R)-2-(Pyridin-2-yloxy)propyl]amino}-methyl)phenyl]ethyl}-methanesulfonamide hydrochloride | 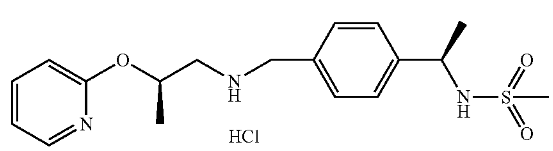 | 364 (M − Cl) | |

TABLE 3-continued

| Ex # | Chemical name | Structure | Physical data MS (m/z): | Chrom. Cond. |
|---|---|---|---|---|
| 3 | N-{(1S)-2,2,2-Trifluoro-1-[4-({[(2R)-2-(pyridin-2-yloxy)propyl]amino}-methyl)phenyl]ethyl}-methanesulfonamide hydrochloride | 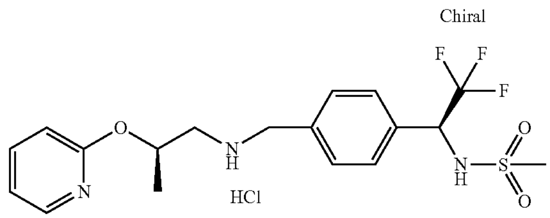 [SMILES: C[C@H](CNCc1ccc([C@H](NS(C)(=O)=O)C(F)(F)F)cc1)Oc1ccccn1 ; Cl] | 418 (M − Cl) | |
| 4 | N-[(1R)-1-{4-[({(2S)-2-[(5-Fluoropyridin-2-yl)oxy]-3-methoxypropyl}amino)-methyl]phenyl]ethyl]-methanesulfonamide hydrochloride | 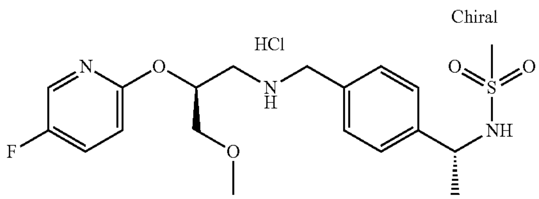 [SMILES: Cl ; COC[C@H](CNCc1ccc([C@@H](C)NS(C)(=O)=O)cc1)Oc1ccc(F)cn1] | 412 (M − Cl) | |
| 5 | N-{(1S)-2,2,2-Trifluoro-1-[4-({[(2S)-3-methoxy-2-(pyridin-2-yloxy)propyl]amino}-methyl)phenyl]ethyl}-methanesulfonamide hydrochloride (1:1) | 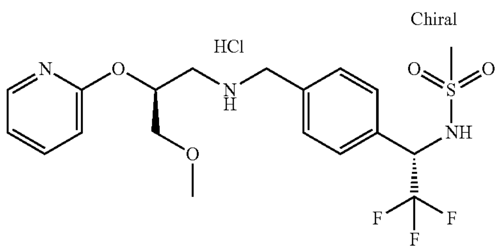 [SMILES: Cl ; COC[C@H](CNCc1ccc([C@H](NS(C)(=O)=O)C(F)(F)F)cc1)Oc1ccccn1] | 448 (M − Cl) | |
| 6 | N-[(1S)-2,2,2-Trifluoro-1-{4-[({(2R)-2-[(5-fluoropyridin-2-yl)oxy]-3-methoxypropyl}amino)-methyl]phenyl}ethyl]-methanesulfonamide hydrochloride | 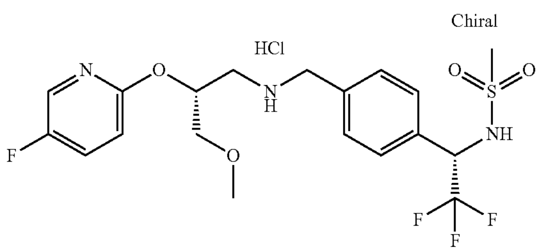 [SMILES: Cl ; COC[C@@H](CNCc1ccc([C@H](NS(C)(=O)=O)C(F)(F)F)cc1)Oc1ccc(F)cn1] | 466 (M − Cl) | |
| 7 | N-{(1S)-2,2,2-Trifluoro-1-[4-({[(2R)-2-(pyridin-3-yloxy)propyl]amino}-methyl)phenyl]ethyl}-methanesulfonamide hydrochloride | 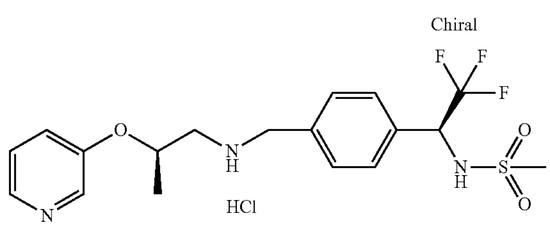 [SMILES: C[C@H](CNCc1ccc([C@H](NS(C)(=O)=O)C(F)(F)F)cc1)Oc1cccnc1 ; Cl] | 417 (M − Cl) | |
| 8 | N-{(1R)-1-[4-({[2-(4-Fluorophenoxy)ethyl]-amino}methyl)phenyl]-ethyl}methane-sulfonamide hydrochloride | 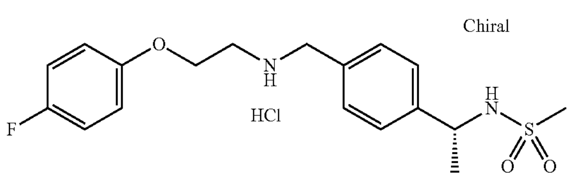 [SMILES: C[C@@H](NS(C)(=O)=O)c1ccc(CNCCOc2ccc(F)cc2)cc1 ; Cl] | 367 (M − Cl) | |

TABLE 3-continued

| Ex # | Chemical name | Structure | Physical data MS (m/z): | Chrom. Cond. |
|---|---|---|---|---|
| 9 | N-[(1R)-1-(4-{[(2-Phenoxyethyl)amino]-methyl}phenyl)ethyl]-methanesulfonamide hydrochloride | (structure, Chiral, HCl) | 349 (M − Cl) | |
| 10 | N-{(1R)-1-[4-({[2-(4-Chlorophenoxy)ethyl]-amino}methyl)phenyl]-ethyl}methane-sulfonamide hydrochloride | (structure, Chiral, HCl) | 383 (M − Cl) | |
| 11 | N-{(1S)-2,2,2-Trifluoro-1-[4-({[2-(4-fluorophenoxy)ethyl]-amino}methyl)phenyl]-ethyl}methane-sulfonamide hydrochloride | (structure, Chiral, HCl) | 421 (M − Cl) | |
| 12 | N-{(1R)-1-[4-({[2-(3,4-Difluorophenoxy)ethyl]-amino}methyl)phenyl]-ethyl}methane-sulfonamide hydrochloride | (structure, Chiral, HCl) | 385 (M − Cl) | |
| 13 | N-{(1R)-1-[4-({[2-(2,4-Difluorophenoxy)ethyl]-amino}methyl)phenyl]-ethyl}methane-sulfonamide hydrochloride | (structure, Chiral, HCl) | 385 (M − Cl) | |
| 14 | N-{(1S)-2,2,2-Trifluoro-1-[4-({[2-(pyridin-2-yloxy)ethyl]amino}-methyl)phenyl]ethyl}-methanesulfonamide hydrochloride | (structure, Chiral, HCl) | 404 (M − Cl) | |

TABLE 3-continued

| Ex # | Chemical name | Structure | Physical data MS (m/z): | Chrom. Cond. |
|---|---|---|---|---|
| 15 | N-[(1R)-1-{4-[({2-[(5-Fluoropyridin-2-yl)oxy]ethyl}amino)-methyl]phenyl}ethyl]-methanesulfonamide hydrochloride | Chiral | 368 (M − Cl) | |
| 16 | N-[(1R)-1-{4-[({2-[(5-Chloropyridin-2-yl)oxy]ethyl}amino)-methyl]phenyl}ethyl]-methanesulfonamide hydrochloride | Chiral | 384 (M − Cl) | |
| 17 | N-[(1S)-2,2,2-Trifluoro-1-{4-[({2-[(5-fluoropyridin-2-yl)oxy]ethyl}amino)-methyl]phenyl}ethyl]-methanesulfonamide hydrochloride | Chiral | 422 (M − Cl) | |
| 18 | N-{(1R)-1-[4-({[2-(4-Methoxyphenoxy)ethyl]-amino}methyl)phenyl]-ethyl}methane-sulfonamide hydrochloride | Chiral | 379 (M − Cl) | |
| 19 | N-{(1R)-1-[4-({[2-(3-Methoxyphenoxy)ethyl]-amino}methyl)phenyl]-ethyl}methane-sulfonamide hydrochloride | Chiral | 379 (M − Cl) | |
| 20 | N-{(1R)-1-[4-({[2-(2-Cyanophenoxy)ethyl]-amino}methyl)phenyl]-ethyl}methane-sulfonamide hydrochloride | Chiral | 374 (M − Cl) | |

TABLE 3-continued

| Ex # | Chemical name | Structure | Physical data MS (m/z): | Chrom. Cond. |
|---|---|---|---|---|
| 21 | N-{(1S)-2,2,2-Trifluoro-1-[4-({[2-(4-fluorophenoxy)-1-(methoxymethyl)ethyl]-amino}methyl)phenyl]-ethyl}methane-sulfonamide hydrochloride, isomer 2 | 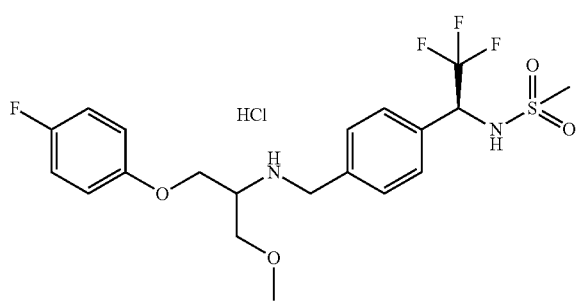 Isomer 2 | 465 (M − Cl) | A |
| 22 | N-{(1S)-2,2,2-Trifluoro-1-[4-({[2-(4-fluorophenoxy)-1-(methoxymethyl)ethyl]-amino}methyl)phenyl]-ethyl}methane-sulfonamide hydrochloride, isomer 1 | 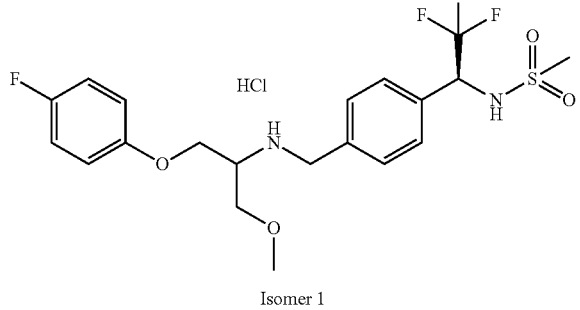 Isomer 1 | 465 (M − Cl) | A |
| 23 | N-{(1R)-1-[4-({[2-(4-Fluorophenoxy)-1-(methoxymethyl)ethyl]-amino}methyl)phenyl]-ethyl}methane-sulfonamide hydrochloride, isomer 1 | 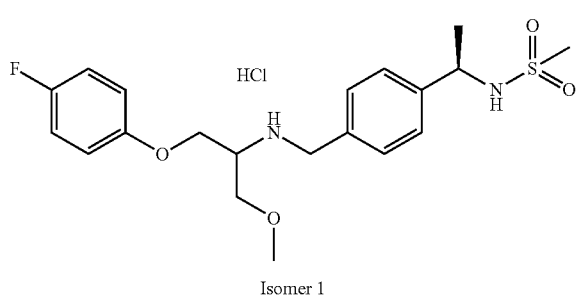 Isomer 1 | 411 (M − Cl) | B |
| 24 | N-[(1S)-2,2,2-Trifluoro-1-{4-[({(2S)-2-[(5-fluoropyridin-3-yl)oxy]-3-methoxypropyl}amino)-methyl]phenyl}ethyl]-methanesulfonamide hydrochloride | 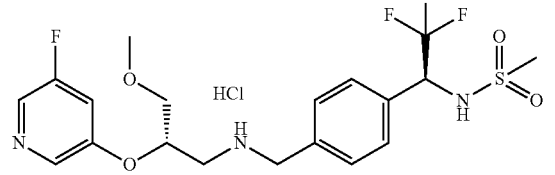 | 466 (M − Cl) | |

TABLE 3-continued

| Ex # | Chemical name | Structure | Physical data MS (m/z): | Chrom. Cond. |
|---|---|---|---|---|
| 25 | N-(1-{4-[({3-Ethoxy-2-[(pyridin-2-yl)oxy]propyl}amino)-methyl]phenyl}ethyl)-methanesulfonamide hydrochloride, isomer 2 | Isomer 2 | 408 (M − Cl) | C |
| 26 | N-[(1R)-1-{4-[({2-Ethoxy-1-[(4-fluorophenoxy)methyl]-ethyl}amino)methyl]-phenyl}ethyl]methane-sulfonamide hydrochloride, isomer 1 | Isomer 1 | 425 (M − Cl) | D |
| 27 | N-[(1S)-2,2,2-Trifluoro-1-{4-[({(1s)-2-[(5-fluoropyridin-2-yl)oxy]-1-methylethyl}amino)-methyl]phenyl}ethyl]-methanesulfonamide hydrochloride | 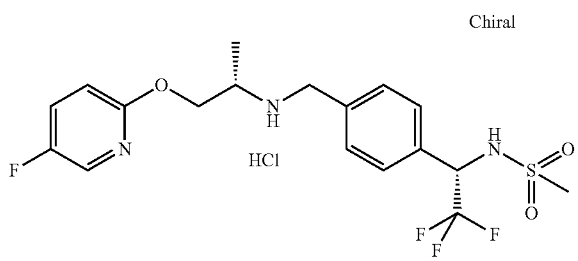 [SMILES: C[C@@H](COc1ccc(F)cn1)NCc1ccc([C@H](NS(C)(=O)=O)C(F)(F)F)cc1 ; Cl] | 436 (M − Cl) | |
| 28 | N-{(1R)-1-[4-({[2-(4-Fluorophenoxy)-3-methoxypropyl]amino}-methyl)phenyl]ethyl}-methanesulfonamide hydrochloride, isomer 2 | Isomer 2 | 411 (M − Cl) | F |
| 29 | N-{(1R)-1-[4-({[2-(4-Fluorophenoxy)-3-methoxypropyl]amino}-methyl)phenyl]ethyl}-methanesulfonamide hydrochloride, isomer 1 | Isomer 1 | 411 (M − Cl) | F |

TABLE 3-continued

| Ex # | Chemical name | Structure | Physical data MS (m/z): | Chrom. Cond. |
|---|---|---|---|---|
| 30 | N-{(1R)-1-[4-({[2-(Pyridin-2-yloxy)butyl]amino}-methyl)phenyl]ethyl}-methanesulfonamide hydrochloride isomer 2 | 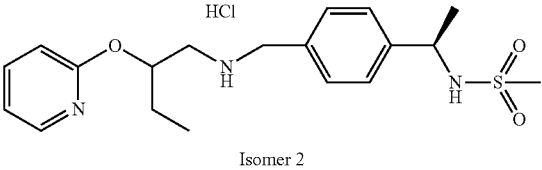 Isomer 2 | 378 (M − Cl) | G |
| 31 | N-[(1R)-1-(4-{[(2-Phenoxypropyl)amino]-methyl}phenyl)ethyl]-methanesulfonamide hydrochloride, isomer 1 | 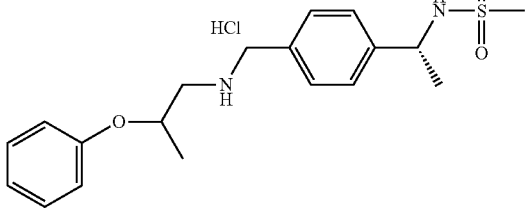 Isomer 1 | 363 (M − Cl) | J |
| 32 | N-[(1R)-1-(4-{[(2-Phenoxypropyl)amino]-methyl}phenyl)ethyl]-methanesulfonamide hydrochloride, isomer 2 | 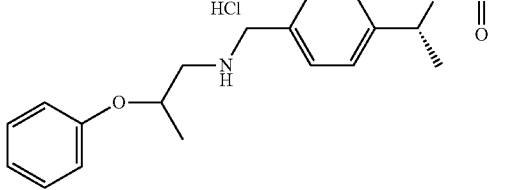 Isomer 2 | 363 (M − Cl) | J |
| 33 | N-[(1R)-1-(4-{[(1-Methyl-2-phenoxyethyl)amino]-methyl}phenyl)ethyl]-methanesulfonamide hydrochloride, isomer 1 | 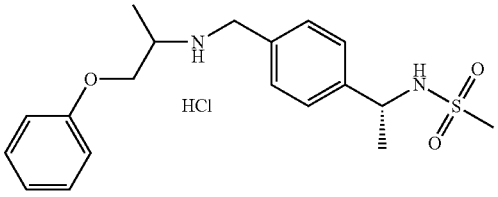 Isomer 1 | 363 (M − Cl) | N |
| 34 | N-[(1R)-1-{4-[({2-[(4-Fluoropyridin-2-yl)oxy]ethyl}amino)-methyl]phenyl}ethyl]-methanesulfonamide hydrochloride | 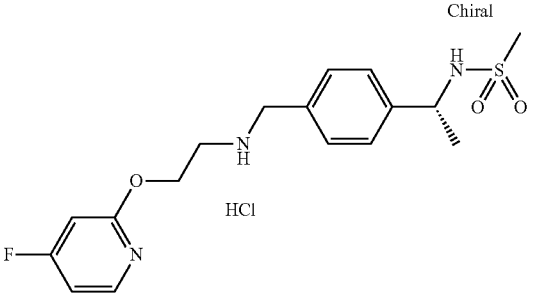 [SMILES: C[C@@H](NS(C)(=O)=O)c1ccc(CNCCOc2cc(F)ccn2)cc1 ; Cl] | 368 (M − Cl) | |

EXAMPLE 35

N-(1-{4-[({3-Ethoxy-2-[(5-fluoropyridin-2-yl)oxy]propyl}amino)methyl]phenyl}ethyl)methanesulfonamide hydrochloride

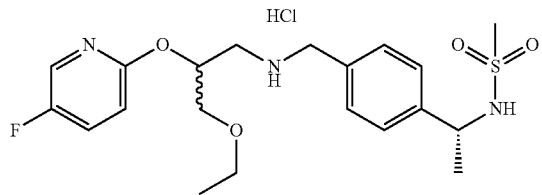 [SMILES: Cl ; CCOCC(CNCc1ccc([C@@H](C)NS(C)(=O)=O)cc1)Oc1ccc(F)cn1]

N-(1-{4-[({3-Ethoxy-2-[(5-fluoropyridin-2-yl)oxy]propyl}amino)methyl]phenyl}ethyl)methanesulfonamide hydrochloride is prepared essentially by method 1 of Example 1 as a mixture of diastereomers. MS (m/z) 426 (M-Cl).

EXAMPLE 36

N-[(1S)-2,2,2-Trifluoro-1-{4-[({(2r)-2-[(5-fluoropyridin-2-yl)oxy]propyl}amino)methyl]phenyl}ethyl]-methanesulfonamide hydrochloride

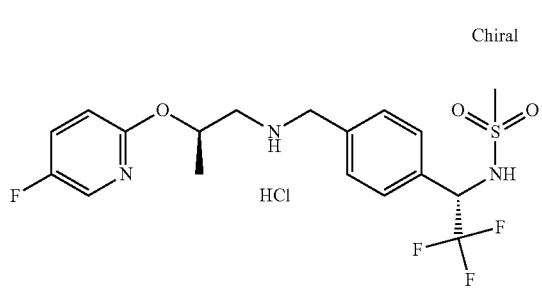 [SMILES: C[C@H](CNCc1ccc([C@H](NS(C)(=O)=O)C(F)(F)F)cc1)Oc1ccc(F)cn1 ; Cl]

Dissolve N-[(1S)-2,2,2-trifluoro-1-[4-[[[(2R)-2-hydroxypropyl]amino]methyl]phenyl]ethyl]methanesulfonamide (1.60 g, 4.70 mmol) in 1,4-dioxane (10 mL) and add sodium hydride (206.8 mg, 5.17 mmol) slowly. Stir at ambient temperature for 20 minutes under a nitrogen atmosphere. Add 2,4-difluoropyridine (540.98 mg, 4.70 mmol) and heat the mixture to 105° C. for 18 hours. Add H$_2$O (100 mL); extract three times with DCM; dry the combined organic extracts over Na$_2$SO$_4$; filter; and concentrate the filtrate under reduced pressure. Purify the residue via silica gel flash column chromatography eluting with 5% (2N NH$_3$/MeOH)/DCM. Concentrate the appropriate fractions under reduced pressure and dissolve the residue (426 mg, 0.98 mmol) in MeOH (10 mL). Add HCl (2M in Et$_2$O, 978.3 uL, 1.96 mmol) and stir at ambient temperature for 5 minutes. Remove the solvent under reduced pressure, and dry in a vacuum oven at 40° C. to give the title compound (460 mg, 99.6%). MS (m/z): 436 (M-Cl).

EXAMPLE 37

N-[(1R)-1-{4-[({(2R)-2-[(5-Fluoropyridin-2-yl)oxy]propyl}amino)methyl]phenyl}ethyl]methanesulfonamide hydrochloride

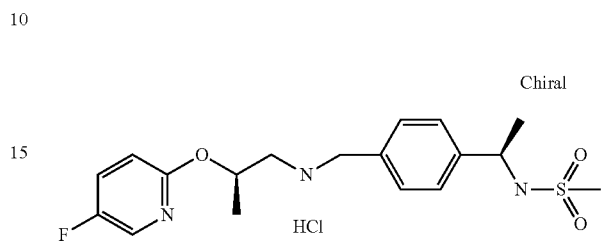

N-[(1R)-1-{4-[({(2R)-2-[(5-Fluoropyridin-2-yl)oxy]propyl}amino)methyl]phenyl}ethyl]methanesulfonamide hydrochloride is prepared essentially by the method of Example 36. MS (m/z) 418 (M-Cl).

EXAMPLE 38

N-[(1S)-2,2,2-Trifluoro-1-{4-[({(2r)-2-[(5-fluoropyridin-3-yl)oxy]propyl}amino)methyl]phenyl}ethyl]methanesulfonamide hydrochloride

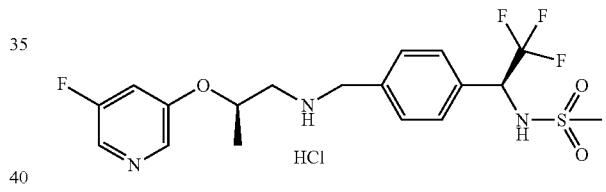

N-[(1S)-2,2,2-Trifluoro-1-{4-[({(2r)-2-[(5-fluoropyridin-3-yl)oxy]propyl}amino)methyl]phenyl}ethyl]methanesulfonamide hydrochloride is prepared essentially by method 1 of Example 36. MS (m/z) 436 (M-Cl).

Chromatography conditions are noted in Table 4 where they vary from the Examples above.

TABLE 4

| Conditions | Column | Column Size | Mobile Phase |
|---|---|---|---|
| A | Chiralpak AD-H | 21 × 250 mm 5 um | CO$_2$/MeOH-IPAm (0.2%) 85/15 |
| B | Chiralpak AD-H | 21 × 250 mm 5 um | CO$_2$/MeOH-IPAm (0.2%) 80/20 |
| C | AY | 30 mm | Hexane/0.1% DEA in EtOH 50/50 |
| D | Chiralpak AD-H | 50 × 250 mm 5 um | CO$_2$/MeOH-DEA (0.1%) 60/40 |
| F | Chiralpak AD-H | 30 × 250 mm 5 um | CO$_2$/MeOH-DEA (0.1%)75/25 |
| G | Chiralcel OJ | 20 × 250 mm 10 um | Hexane/0.2% DMEA in EtOH 75/25 |
| J | Chiralpak AD-H | 21 × 150 mm 5 um | CO$_2$/MeOH-IPAm (0.2%) 70/30 |
| N | Chiralpak AD-H | 20 × 250 mm 10 um | 100% MeOH-DMA(0.2%) |

EXAMPLE 39

Crystalline N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide hydrochloride

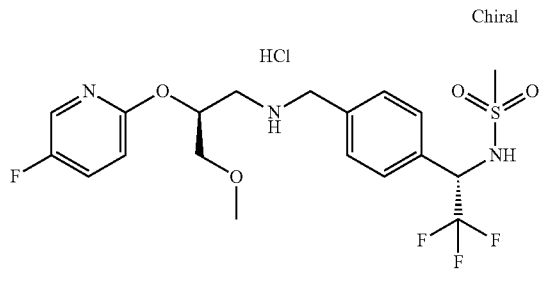

Dissolve 175.24 g of N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide (Example 1) in 470.29 mL of EtOH. Cool this solution to 10° C. Add 1.25 equivalents of HCl slowly via a dropping funnel, and allow the solution to warm to room temperature. Collect the resulting solids by filtration and dry at 60° C. overnight in the vacuum oven to give 150.97 g of the titled compound in 89.36% yield.

X-Ray Powder Diffraction

The X-ray diffraction (XRD) patterns of crystalline N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride (Example 39) solids can be obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. In the present case, a peak position variability of 0.2 in 2θ will take into account these potential variations without hindering the unequivocal identification of the indicated crystal form. Confirmation of a crystal form may be made based on any unique combination of distinguishing peaks (in units of °2θ). (United States Pharmacopeia #35, National Formulary #30, Chapter 941, pages 427-432, (2012). The crystal form diffraction patterns, collected at ambient temperature and relative humidity, were adjusted based on NBS standard reference material 675 (mica) with peaks at 8.853 degrees 2-theta.

Crystalline HCl

A prepared sample of the crystalline N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide hydrochloride Dissolve 175.24 g of N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide is characterized by an X-ray diffraction pattern using CuKa radiation as having diffraction peaks (2-theta values) as described in Table 5 below, and in particular having peaks at 21.14 in combination with one or more of the peaks selected from the group consisting of 18.13, 14.95, and 18.67; with a tolerance for the diffraction angles of 0.2 degrees.

TABLE 5

X-ray powder diffraction peaks of the crystalline N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride

| Peak | Angle (°2-Theta) | Relative Intensity (% of most intense peak) |
|---|---|---|
| 1 | 5.46 | 28.3 |
| 2 | 6.17 | 25.6 |
| 3 | 11.10 | 37.1 |
| 4 | 12.71 | 54.9 |
| 5 | 13.97 | 42.1 |
| 6 | 14.95 | 64.8 |
| 7 | 18.13 | 71.7 |
| 8 | 18.67 | 60.5 |
| 9 | 21.14 | 100 |
| 10 | 27.76 | 45.8 |

MOGAT-2 Inhibitory Assay

The in vitro inhibitory activity of compounds against human MOGAT-2 is evaluated in this assay. MOGAT-2 transfers an oleoyl group to monooleoyl-glycerol ("MAG") from oleoyl-CoA to form dioleoyl-glycerol ("DAG") in the intestinal triglyceride resynthesis pathway. The assay takes advantage of Microscint Extraction, which extracts hydrophobic molecules selectively over hydrophilic ones to separate the $^{14}$C-oleoyl-CoA from $^{14}$C-DAG.

Genetically engineered insect SF9 cells express human MOGAT-2. Prepare the cell lysate in 20 mM of NaCl with protease inhibitor (Roche Cat #11873580001). Homogenize the SF9 cells expressing human MOGAT-2 at 15,000 rpm for 20×2 seconds (PT-3100 Polytrone). Centrifuge the homogenate at 1000 g for 10 minutes at 4° C. Collect the supernatant into a separate tube for protein quantification and activity testing. Purify the glycerol monooleate substrate (Spectrum Chemical, CAS#25496-72-4) chromatographically. Prepare the monoacylglycerol (MAG) substrate in phospholipid vesicles (dioleoyl phosphatidylcholine "DOPC"). Prepare the MAG/DOPC vesicles at 20 mM concentration of total lipids (MAG and DOPC). Prepare different molar ratios of MAG to total lipids for either compound screening (8.9%) or compound kinetic studies (2.6-40%). Mix the appropriate amount of purified MAG and DOPC (Avanti Polar Lipids #850375C) in chloroform in a glass tube. Subsequently, evaporate chloroform under stream of $N_2$ gas and then dry under reduced pressure for 30 minutes. Add an appropriate amount of buffer (Tris-Cl pH 7.4, 250 mM sucrose, 1 mM EDTA) to the dried MAG/DOPC mixture for the desired total lipid concentration. Sonicate the MAG/DOPC solution until the solution is clear. Measure the vesicle size using dynamic light scattering to confirm uniformity.

The assay buffer consists of 100 mM Tris, pH 7.5 (Invitrogen 15567-022), 11% DMSO, 250 mM sucrose (Sigma S-0389), 1 mM, EDTA, and Complete Protease Inhibitor cocktail (Roche Diagnostic 12454800). Add the test compounds to the buffer together with the substrates and enzymes. The final concentration for the reaction is 0.016 mg/mL SF9 cell extract, 20 μM oleoyl-CoA (3.5 μM $^{14}$C-oleoyl-CoA), 1.26 mM total lipid in the form of sonicated vesicles, composed of 8.9:91.1 (molar ratio) MAG:DOPC. Stop the reaction after 90 minutes of incubation at room temperature by adding AESSM (12.5% of 100% denatured EtOH; 11% DI H2O; 2.5% 1.0N NaOH; 59% Isopropanol (Mallinckrodt 3031-08); 15% Heptane (Omni Solv HX0078)), by volume. Add Microscint E and then seal the plates and count on a scintillation counter after at least 4 hours of equilibration at room temperature. Calculate the $IC_{50}$ (concentration to reach half maximum inhibition) using Excel Fit software (version 4; Data analyzing using a 4-parameter non-linear logistic equation (ABase Equation 205)) by plotting concentration vs relative MOGAT-2 activity.

All the compounds exemplified herein exhibit an $IC_{50}$ of 50 nM or less in this MOGAT-2 in vitro inhibitory assay and Example 1 exhibits an $IC_{50}$ of 2 nM. The results demonstrate that the exemplified compounds are inhibitors of the MOGAT-2 in this assay.

Inhibitory Activity in MOGAT-2 Cell Assay

The inhibitory activity of compounds against human MOGAT-2 in a cell environment is evaluated in this assay. Caco-2 is a human colon carcinoma cell line and is often used as a model for intestinal epithelial cells. Caco-2 does not express MOGAT-2, and, thus, human MOGAT-2 is engineered into the cell line through a stable transfection. A MAG analogue, 2-O-Hexadecylglycerol (HDG), is utilized to detect cellular MOGAT-2 activity, because HDG is not hydrolyzed and the resulting product is readily monitored by mass spectrometry. The substrate is delivered to cells using as a mixture with DOPC in the form of sonicated vesicles.

Seed the Caco2 cells onto 100 mm dishes to be 80% confluent after 24 hours in complete media (3/1 DMEM: F12+ 10% FBS+20 mM HEPES+gentamicin). Transfect the cells with hMOGAT-2 plasmid (MOGAT-2-pcDNA3.1-Hygro) using Lipofectamine 2000 (Invitrogen). After a 6 hour exposure to the transfection mixture, wash the cells three times in PBS and then add media. Incubate the cells for an additional 18 hours incubation, trypsinize the cells and serially dilute them into 100 mm dishes. Add complete media+400 µg/ml hygromycin and incubate until clones appear. Isolate and transfer the clones into 24 well dishes and grow to confluency. Prepare the RNAs from these clones using a Qiagen RNAeasy kit. Perform Taqman analysis using an ABI inventoried assay (HS00228262) on a 7900 Sequence Detection System (ABI). Analyze the lysates from these clones by Western blot analysis using a goat polyclonal antibody (Santa Cruz, SC-32392 to confirm human MOGAT-2 expression of a 38 kD protein corresponding to MOGAT-2.

Mix 2-O-hexadecylglycerol ("HDG", Biosynth Chemistry & Biology, #H-1806, 562.7 µl of 20 mg/ml) and DOPC (14.3 ml of 20 mg/ml) in chloroform in a glass tube; dry first under $N_2$ gas; and then under reduced pressure for additional 30 minutes. Add 20 ml of buffer (150 mM Tris-Cl pH 7.4, 250 mM sucrose, 1 mM EDTA) to the dried HDG/DOPC mixture while sonicating until the solution becomes clear. Plate the Caco2 cells into a poly-D-lysine coated 96-well plate (the "Cell Plate") at 37° C., 5% $CO_2$ overnight. Remove the growth media and pretreat the cells with the test compound in DMEMF12 (3:1) media (GIBCO 93-0152DK) containing 2% BSA (Sigma) for 30 minutes. Treat the cells with one test compound in 2% BSA DMEMF12 (3:1) media containing 40 µM of oleic acid and 800 µM of 8.9:91.9 (molar ratio) HDG/DOPC for 4 hours. Trypsinize the cells with 50 µl of trypsin solution and add 50 µl of PBS. Immediately freeze the cells on dry ice and store at −20° C. for LC-MS analysis. Extract the cells with chloroform/methanol as follows: transfer the cells to a 2 ml plate; wash the cell plate with 200 µL methanol and then transfer the methanol wash to the 2 ml plate; wash the cell plate again with 200 µL PBS and transfer the PBS wash to the 2 ml plate. Add chloroform (400 µL) with internal standard (19.52 ng/mL) DAG (15:0, 15:0 (Sigma)), D5-TAG (39.03 ng/mL) CDN (16, 16, 16) to the 2 mL Plate. Turn the sealed 2 mL Plate up and down (10×), then vortex and spin. Remove 400 µL of the lower layer from the 2 mL plate and add to the wells of another plate the "Final Plate". Add $CHCl_3$:MeOH (400 µL 2:1) to the 2 mL Plate. Again turn the sealed 2 mL Plate up and down (10×), vortex and spin. Remove 220 µL of the lower layer from the 2 mL Plate and add to the Final Plate. Dry the Final Plate and reconstitute with 500 mL of IPA. Seal the Final Plate and shake for 5 min. Inject 10 µA of a sample from the Final Plate onto a Halo C8 column (2.1×50, 2.7 uL particle size) held at 60° C. using a Leap auto sampler with a 10 µL loop, interfaced to a Shimadzu solvent delivery system. Monitor the channels to collect data for the D5 C16 TAG internal standard as well as the ether TAG, and C52 and C54 natural TAGs. Solvent A is 80/20 $H_2O$/Methanol with 20 µM ammonium acetate. Solvent B is 50/50 IPA/THF with 20 µM ammonium acetate. Flow rate is 0.4 mL/min. Wash solvents were $H_2O$/MeOH and DCM. Using Xcalibur software extract the areas of the peaks of interest, and export the data to Excel which uses the following formula: (area of ether TAG/area of C54 natural TAG)/Area of IS. This ratio effectively accounts for variance of cell number in each well. The results for this MOGAT-2 cell based assay are provided below in Table 6. The results of the MOGAT-2 cell based assay demonstrate that the Examples listed in Table 6 inhibit the human MOGAT-2 in the cell environment.

TABLE 6

| Example | $IC_{50}$ nM (Std Dev., n*) |
| --- | --- |
| 1 | 30.6 (8.1, n = 7) |
| 3 | 14.4 (n = 1) |
| 5 | 44.6 (25.9, n = 4) |
| 17 | 45.5 (7.6, n = 5 |
| 36 | 36.1 (25.6, n = 8) |

*n is the number of experiments.

Pharmacological Effects in a Dog Oil Bolus Model

Inhibiting MOGAT-2 found in the small intestine may be useful for treating hypertriglyceridemia caused by excessive fat intake Inhibition of MOGAT-2 disrupts resynthesis of triglycerides, which reduces secretion of triglycerides from the intestine. Therefore, MOGAT-2 inhibition interferes with a specific process that leads to eventual secretion of triglycerides into the intestine for eventual circulation through the body. To assess the ability of one or more of the exemplified compounds to inhibit MOGAT-2 induced TAG secretion into the intestine as measured in the blood system, the following protocol can be followed.

Twenty one male beagles (n=7 per treatment group) are enrolled for each study, each dog selected to have a body weight between 9-13 kg. House the dogs in cages with a standard light cycle (12 hours light and 12 hours dark); at room temperature: 72±8° F.; and at 30%-70% relative humidity. Fast the dogs for 16 hours prior to the start of the study, then dose the fasted dogs with vehicle (1% HEC, 0.25%, Tween 80, Antifoam) or one of the test compounds in that vehicle. Bleed the dogs one hour after dosing, (0.5 ml from the jugular vein) for a time 0 sample. Dose the dogs with olive oil (Sigma Catalog#: O-1514, 5 ml/kg) immediately after collection of the time 0 sample. Collect samples into an EDTA tube on ice at 1.5, 2, 3, 5, 7, and 9 hrs post compound/vehicle dosing. Centrifuge the samples at 9000 cpm for 15 min and analyze (Roche Cat no. 1877771) for plasma total triglyceride using a Roche Hitachi 917. For plasma TAG 18.1_18.1_18.1 measurement, extract the samples and perform LC/MS/MS analysis similarly to that described above in MOGAT-2 Cell Assay using 10 μL of plasma/.

The analyte is the [M+NH4]+ ion of TAG 18:1 18:1 18:1, which has a mass of 902.8 m/z; the internal standard is D5 TAG 16:0 16:0 16:0, which has a mass of 829.8 m/z. Report the ratio of the 603.5 m/z daughter ion of 902.8 m/z (TAG 18:1 18:1 18:1) and the 556.5 m/z daughter ion of 829.8 m/z (D5 TAG 16:0 16:0 16:0 internal standard) changes in TAG 18:1 18:1 18:1 relative amount. Calculate the net plasma TAG AUC from total TAG AUC minus baseline TAG AUC using Graphpad Prism4: (Net $AUC_{TAG}=AUC_{TAG}$ post oil bolus–$AUC_{TAG}$ at 0 hour). The percent inhibition of plasma triglyceride is calculated as follows: the (oil bolus group mean of net TAG AUC–oil bolus group mean of net TAG AUC with compound treatment/oil bolus group mean of net TAG AUC) *100. The final statistic analysis uses Dunnett's method of One way Anova for comparison with the control. All Net TAG AUC values are transformed to ranked averaged AUC for comparison to limit the variability within the studies.

Example 1 dosed at 30 mg/kg reduced TAG secretion in the intestine by 61% (64% of 18:1 TAG) and at 60 mg/kg reduced TAG absorption by 77% inhibition (76% 18:1 TG). Example 36 dosed at 60 mg/kg reduced TAG secretion by 38% (43% of 18:1 TAG). These data demonstrate that Examples 1 and 36 inhibits MOGAT-2 activity for TAG secretion from the intestine.

The exemplified compounds of the present invention can be readily formulated into pharmaceutical compositions in accordance within accepted practices such as found in Remington's Pharmaceutical Sciences, Gennaro, Ed., Mack Publishing Co. Easton Pa. 1990. A treating physician or other medical person will be able to determine an effective amount of the compound for treatment of a person in need, particularly for the treatment of hypertriglyceridemia. Preferred pharmaceutical compositions can be formulated as a tablet or capsule for oral administration. The tablet or capsule can include a compound of the present invention in an effective amount for treating a patient in need of treatment.

What is claimed is:

1. A compound of the formula below:

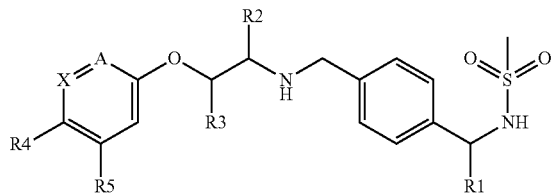

wherein
R1 is selected from: —CH$_3$ and —CF$_3$;
R2 is selected from: H, —CH$_3$, —CH$_2$OCH$_3$, and —CH$_2$OCH$_2$CH$_3$;
R3 is selected from: H, —C$_{1-2}$ alkyl, —CH$_2$OCH$_3$, —CH$_2$OCH$_2$CH$_3$;
R4 is selected from: H, halo, and —OCH$_3$;
R5 is selected from H and halo;
A is selected from: CH, CF, C—CN, and N;
X is selected from: CH, CF, COCH$_3$, and N; and
provided that only one of X and A is N,
or a pharmaceutically acceptable salt thereof.

2. A compound according to claim 1 wherein R1 is —CH$_3$.
3. A compound according to claim 1 wherein R1 is —CF$_3$.
4. A compound according to claim 1, wherein R2 is selected from: H, —CH$_3$, —CH$_2$OCH$_3$.

5. A compound according to claim 4 wherein R2 is H.
6. A compound according to claim 1 wherein R3 is selected from: H, —CH$_3$, —CH$_2$OCH$_3$, and —CH$_2$OCH$_2$CH$_3$.
7. A compound according to claim 6 wherein R3 is selected from: H, —CH$_2$OCH$_3$, and —CH$_2$OCH$_2$CH$_3$.
8. A compound according to claim 7 wherein R3 is —CH$_2$OCH$_3$.
9. A compound according to claim 1 wherein R4 is selected from: H and F.
10. A compound according to claim 9 wherein R4 is F.
11. A compound according to claim 1 wherein R5 is H.
12. A compound according to claim 1 wherein A is selected from CH or CF.
13. A compound according to claim 1 wherein A is N.
14. A compound according to claim 1 wherein X is CF or N.
15. A compound according to claim 1 wherein X is CH.
16. A compound of according to claim 1 wherein the pharmaceutically acceptable salt is a hydrogen chloride addition salt.
17. A pharmaceutical composition comprising a compound according to claim 1, or a pharmaceutically acceptable salt thereof, and at least one of a pharmaceutically acceptable carrier, diluent, or excipient.
18. A compound of the formula below:

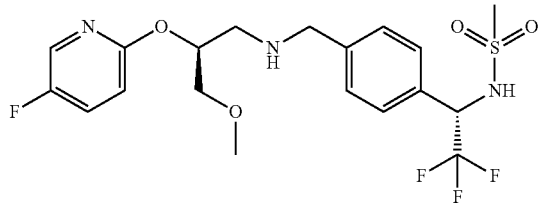 [SMILES: COC[C@H](CNCc1ccc([C@H](NS(C)(=O)=O)C(F)(F)F)cc1)Oc1ccc(F)cn1]

or a pharmaceutically acceptable salt thereof.
19. A compound which is N-[(1S)-2,2,2-Trifluoro-1-{4-[({(2S)-2-[(5-fluoropyridin-2-yl)oxy]-3-methoxypropyl}amino)methyl]phenyl}ethyl]methanesulfonamide hydrochloride.
20. A pharmaceutical composition comprising N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide, or a pharmaceutically acceptable salt thereof, and at least one of a pharmaceutically acceptable carrier, diluent, or excipient.
21. A compound which is N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form characterized by an X-ray powder diffraction pattern obtained from a CuKα source λ=1.54056 Å), which comprises peaks at:
a) 12.71°, 14.95°, 18.13°, 18.67°, 21.14° and 27.76°±/−0.2 in 2θ or
b) 5.46°, 11.10°, 12.71°, 13.97°, 14.95°, 18.13°, 18.67°, 21.14°, and 27.76°±/−0.2° in 2θ.
22. A composition comprising greater than 80% w/w N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form according to claim 21.
23. A composition comprising greater than 95% w/w N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form according to claim 21.

24. A pharmaceutical composition comprising N-[(1S)-2,2,2-Trifluoro-1-{4-[({(2S)-2-[(5-fluoropyridin-2-yl)oxy]-3-ethoxypropyl}amino)methyl]phenyl}ethyl]methanesulfonamide hydrochloride salt in crystalline form according to claim 21 and at least one of a pharmaceutically acceptable carrier, diluent, or excipient.

25. A method of treating a patient in need of treatment for hypertriglyceridemia, the method comprises administering to the patient an effective amount of a compound, according to claim 1, or a pharmaceutically acceptable salt thereof.

26. A method of treating a patient in need of treatment for hypertriglyceridemia, the method comprises administering to the patient an effective amount of a compound according to claim 18, or a pharmaceutically acceptable salt thereof.

27. A method of treating a patient in need of treatment for hypertriglyceridemia, the method comprises administering to the patient an effective amount of a pharmaceutical composition according to claim 24.

* * * * *